United States Patent [19]

Noguchi et al.

[11] 4,001,297
[45] Jan. 4, 1977

[54] THIOUREIDOBENZENE PREPARATIONS AND USES THEREOF

[75] Inventors: Teruhisa Noguchi, Tokyo; Kimpei Kato, Ohiso; Koshin Miyazaki, Odawara, all of Japan

[73] Assignee: Nippon Soda Company, Ltd., Tokyo, Japan

[22] Filed: Oct. 15, 1974

[21] Appl. No.: 514,453

Related U.S. Application Data

[63] Continuation-in-part of Ser. No. 832,425, June 11, 1969, abandoned.

[30] Foreign Application Priority Data

| June 18, 1968 | Japan | 43-41588 |
| Oct. 12, 1968 | Japan | 43-73914 |
| Nov. 2, 1968 | Japan | 43-79655 |
| Nov. 5, 1968 | Japan | 43-80379 |
| Nov. 18, 1968 | Japan | 43-83999 |
| Dec. 9, 1968 | Japan | 43-89523 |

[52] U.S. Cl. .............. 260/470; 424/309; 424/322
[51] Int. Cl.² .......................... C07C 149/40
[58] Field of Search ................... 260/470

[56] References Cited

UNITED STATES PATENTS

| 3,843,715 | 10/1974 | Widdig | 260/470 |
| 3,855,272 | 12/1974 | Girandon | 260/470 |
| 3,927,069 | 12/1975 | Adams | 260/470 |

FOREIGN PATENTS OR APPLICATIONS

| 1,214,415 | 12/1970 | United Kingdom | 260/470 |

Primary Examiner—Howard T. Mars
Attorney, Agent, or Firm—Howson and Howson

[57] ABSTRACT

The compounds of the general formula:

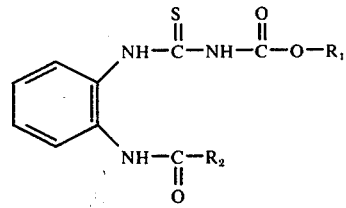

wherein $R_1$ is alkyl of 1 through 4 carbon atoms,
$R_2$ is cyclopropyl or phenyl; have fungicidal and acaricidal activities.

3 Claims, No Drawings

THIOUREIDOBENZENE PREPARATIONS AND USES THEREOF

This application is a continuation-in-part of our pending application Ser. No. 832,425 filed June 11, 1969 and now abandoned.

DETAILED DESCRIPTION OF THE INVENTION

This invention relates to novel substituted thioureidobenzenes and to a process for the preparation of the same. Further, the invention relates to fungicial and acaricidal compositions containing one or more of said novel compounds and further includes methods for combatting fungi and mites with the same compounds.

Particularly in the recent years, agricultural chemicals have been developed remarkably and numbers of fungicides are present. Thereby, a number of diseases, which have been hitherto regarded as incontrollable, have gradually been decreased. But, because of absence of suitable fungicides, some diseases remain and give serious damage to plants year by year, so that development of effective fungicides are intensively desired.

Further, mites give a great deal of damage to plants and some mites resist against acaricide by employing the one continuously. In order to control these mites, development of effective acaricides are intensively desired.

The inventors have discovered that applications of the compounds of this invention, surprisingly, entirely protects or reduces damage to plants due to both fungi and mites with a small amount.

The novel compounds in the present invention are characterized by the following formula:

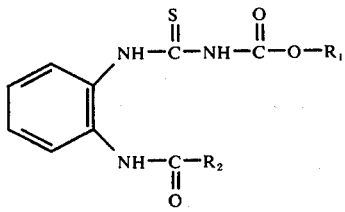

wherein
$R_1$ is alkyl of 1 through 4 carbon atoms;
$R_2$ is cyclopropyl or phenyl.

The compounds of this invention have superior fungicidal and acaricidal activity.

The many fungi against which the compounds of this invention are active may be represented by, but it is not intended to be limited to, the following: *Botrytis cinerea, Cercospora beticola, Cladosporium fulvum, Collectotrichum lagenarium, Corynespora melongenae, Elsinoe fawcetti, Glomerella cingulata, Helminthosporium signoideum, Mycosphaerella pomi, Pellicularia sasaki, Penicillium spp., Phaeoisariopsis vitis, Piricularia oryzae, Podosphaera leucotricha, Pseudoperonospora humuli, Sclerotinia cinerea, Sclerotinia sclerotiorum, Sphaerotheca fuliginea, Sphaerotheca humili, Venturia inaequalis.*

The compounds of this invention have superior mite ovicidal activity against mites such as *Panonychus citri, Panonychus ulmi, Tetranychus desertorum, Tetranychus urticae.*

It is an advantage of the invention that the compounds of this invention have very low mammalian toxicity.

The compounds of this invention can be prepared by the reaction illustrated below, wherein $R_1$ and $R_2$ are defined as above:

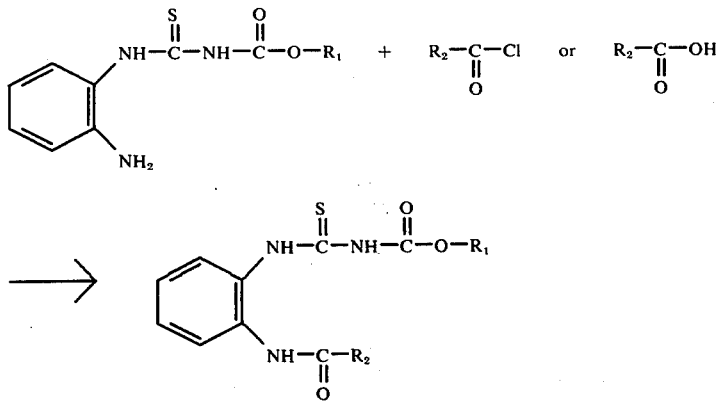

The reaction described in above can be carried out by reacting one of 2-(3-alkoxycarbonyl-2-thioureido)-anilines with one of acids, and acyl chlorides without solvent or in an inert organic solvent such as acetone, methylethylketone, methanol, ethanol, dioxane, benzene or toluene.

In order to facilitate a clear understanding of the invention, the following preferred specific embodiments are described as illustrative and not as limiting the invention.

EXAMPLE 1

1-Cyclopropancarboamide-2-(3-methoxycarbonyl-2-thioureido)-benzene 3.5g (0.033 mole) of cyclopropylcarbonylchloride were added slowly to 5.6g (0.025 mole) of 1-(2-aminophenyl)-3-methoxycarbonyl-2-thiourea in 30ml of tonuene at room temperature under agitation and the mixture was kept on reflux condition for an hour. The reaction mixture was cooled to room temperature and filtered with suction. The recovered colorless crystals were washed with water and dried. Then, by recrystallization of the crystals from the mixture of methanol and acetone, 4.2g of the crystals having the decomposition point of 191° – 192° C. were obtained.

EXAMPLE 2

1-Benzamido-2-(3-ethoxycarbonyl-2-thioureido)-benzene 3.5g (0.02 mole) of acetyl chloride were added slowly to 5.3g (0.02 mole) of 1-(2-aminophenyl)-3-ethoxycarbonyl-2-thiourea in 50ml of toluene at room temperature under agitation, and the mixture was dept on reflux condition for three hours. 6g (0.02 mole) of crude crystals of 1-benzamide-2-(3-ethoxycarbonyl-2-thioureido)-benzene having a decomposition point of 190° C. were obtained following the procedure of Example 1.

By recrystallization from a mixture of acetone with methanol, the decomposition point of the crystals raised from 190° C. to 193° C. The elementary analysis values of the crystals (molecular formula $C_{17}H_{17}N_3H_3S$) were indicated as follows:

| Element | Observed value | Calculated value |
|---|---|---|
|  | % | % |
| C | 59.60 | 59.48 |
| H | 4.92 | 4.96 |
| N | 12.18 | 12.24 |

The compounds of the present invention possess very superior fungicidal and acaricidal activity compared to known compounds.

In this invention usually a small but effective amount of the compounds is applied to plant surface by spraying, drenching or dusting to protect or control fungi, diseases, mites or mite eggs. The concentrations of the active ingredients in the fungicidal or acaricidal compositions of this invention vary according to type of formulation, and they are, for example, used in a range of 5 – 80 weight percent, preferably 10 – 60 weight percent, in wettable powder, 5 – 70 weight percent, preferably 10 – 50 weight percent, in emulsifiable concentrates, and 0.5 – 10 weight percent, preferably 1 – 5 weight percent in dust formulations.

In the above formulation of the composition, auxiliary agents or materials, for example, inert mineral powders such as clay, talc and diatomaceous earth, dispersing agents such as sodium lignin sulfonate and casein, and wetting agents such as alkylarylsulfonate and polyoxyethylene alkylphenol, may be employed according to the type of the formulation for combatting fungi, bacteria and mites. Furthermore, the composition may be applied as a mixture with other fungicides, insecticides, acaricides, plant growth regulators and fertilizers.

The non-limiting examples for the fungicidal or acaricidal compositions are illustrated as follows:

EXAMPLE 3

Wettable Powder

| | Parts by Weight |
|---|---|
| Compound of Example 1 | 20 |
| Sodium alkylsulfonate | 5 |
| Diatomaceous earth | 75 |

These are mixed and micronized in jet pulverizer to a particle size of 10 – 30 microns. In practical use, the micronized mixture is diluted to a concentration of 0.01 to 0.05% of active ingredient with water. The suspension is applied as spray or drench.

EXAMPLE 4

Emulsifiable Concentrate

| | Parts by Weight |
|---|---|
| Compound of Example 2 | 10 |
| Alkylaryl polyoxyethylene | 5 |
| Dimethylformamide | 50 |
| Xylene | 35 |

These were mixed and dissolved. In practical use, the solution is diluted with water to a concentration of 0.01 to 0.05% of active ingredient and this suspension is sprayed or used for drenching.

EXAMPLE 5

Dust Formulation

| | Parts by Weight |
|---|---|
| Compound of Example 1 | 5 |
| Talc | 94.9 |
| Alkylaryl polyoxyethylene | 0.1 |

These were mixed and crushed to fine powder. The dust formulation is usually applied as dusting powder at a rate of 3 to 5kg per are.

In the Example 3–5, it is not intended to limit the emulsifying, wetting or dispersing agents, carriers and solvents to the ones described by way of illustration.

The superior fungicidal and acaricidal effects of the novel compounds of this invention are clearly illustrated by the following tests.

TEST 1

Test for Control of Rice Blast Disease

The compounds to be tested were applied as water-diluted solution of wettable powder prepared according to the method of Example 3. The potted rice plants grown to a 3 leaf stage were sprayed at a rate of 25 cc/pot with solutions of the test materials. One day later, the plants were inoculated with a spore suspension of rice blast fungus, *Piricularia oryzae*, and held under the condition of incubation (at about 100% relative humidity and 26° C.) in a wet cabinet for 24 hours. Then, the plants were moved to a greenhouse bench. Ten days after incubation, number of lesions per pot were examined and evaluation of percent disease control was based upon the percentage of lesions occuring on the untreated check. The results are shown in Table 1.

TABLE 1

| Compound | Conc. of active ingredient (γ/ml) | Average Control value (%) |
|---|---|---|
| Ph-NH-C(=S)-NH-C(=O)-O-CH₃ / Ph-NH-C(=O)-cyclopropyl-H | 500 | 98.2 |
| Ph-NH-C(=S)-NH-C(=O)-O-C₂H₅ / Ph-NH-C(=O)-Ph | 500 | 96.2 |
| Control (Rabiden) | — | 0 average number of lesion per pot is 167 |

TEST 2

Test for Control of Rice Sheath Blight Disease

The compounds to be tested were applied as water-diluted solution of wettable powder prepared by the method of Example 7. The potted rice plants (24 – 25 plants per single pot) grown to a 5 leaf stage were sprayed at a rate of 25 cc/pot with solution of the test material. Two days later, the plants were inoculated with mycelia of the rice sheath blight fungus, *Corticium sasaki*, grown in a culture medium. The plants were transferred to a wet cabinet and held under the condition of incubation (at 100% relative humidity and 25° – 30° C.) for two days. At the end of this time, the plants were moved to a greenhouse bench. Seven days after incubation, number of plants infected were examined in each testpot and the data were recorded as the control value. The results are shown in Table 2.

TABLE 2

| Compound | Conc. of active ingredient (γ/ml) | Average Control value (%) |
|---|---|---|
| Ar-NH-C(=S)-NH-C(=O)-O-CH₃ / Ar-NH-C(=O)-cyclopropyl-H | 500 | 98.4 |
| Ar-NH-C(=S)-NH-C(=O)-O-C₂H₅ / Ar-NH-C(=O)-Ph | 500 | 94.2 |
| Control (Rabiden) | — | 0 (Average disease index is 3.792) |

TEST 3

Test for Control of Tetranychus mite

About 30 adult female mites of Tetranychus mite (*Tetranychus desertorum*) laid on main leaves of the potted kidney bean plants grown 7 to 10 days stage after sprouting. One day later, the wounded mites were removed from the plants. The compounds to be tested were sprayed on the plants as water suspension containing 0.05% of the compound prepared by the method Example 4. After 3 days from spraying, the surviving adult mites were removed. The viability of eggs deposited during this period was examined after 14 days from spraying.

Ovicidal activity is calculated by the following:

$$\text{Ovicidal activity (\%)}: \frac{(a-b)}{a} \times 100$$

a: numbers of eggs deposited
b: numbers of hatched eggs

But, rating of ovicidal activity was recorded as follows:

| Ovicidal activity | Rating |
|---|---|
| 100% | +++ |
| 80 – 90% | ++ |
| 50 – 79% | + |
| 0 – 49% | − |

The results are shown in Table 3.

TABLE 3

| Compound | Rating Ovicidal activity |
|---|---|
| phenyl ring with NH–C(=S)–NH–C(=O)–O–CH$_3$ and NH–C(=O)–cyclopropyl substituents | ++ |
| phenyl ring with NH–C(=S)–NH–C(=O)–O–C$_2$H$_5$ and NH–C(=O)–phenyl substituents | ++ |

We claim:

1. A compound of the formula

[structure: ortho-disubstituted benzene with NH–C(=S)–NH–C(=O)–O–R$_1$ and NH–C(=O)–R$_2$]

wherein R$_1$ is alkyl of 1 through 4 carbon atoms; R$_2$ is cyclopropyl or phenyl.

2. A compound of the formula

[structure: ortho-disubstituted benzene with NH–C(=S)–NH–C(=O)–O–CH$_3$ and NH–C(=O)–cyclopropyl]

3. A compound of the formula

[structure: ortho-disubstituted benzene with NH–C(=S)–NH–C(=O)–O–C$_2$H$_5$ and NH–C(=O)–phenyl]

* * * * *